(12) United States Patent
Cunningham et al.

(10) Patent No.: US 10,639,048 B2
(45) Date of Patent: May 5, 2020

(54) SURGICAL DRILL GUIDE SYSTEM WITH ARTICULATING GUIDE ADAPTOR

(71) Applicant: Smith & Nephew, Inc., Memphis, TN (US)

(72) Inventors: Matthew Dennis Cunningham, Lakeville, MA (US); Stephen Santangelo, Sturbridge, MA (US); Kimberly Anne Baker, Cambridge, MA (US)

(73) Assignee: Smith & Nephew, Inc., Memphis, TN (US)

( * ) Notice: Subject to any disclaimer, the term of this patent is extended or adjusted under 35 U.S.C. 154(b) by 355 days.

(21) Appl. No.: 15/828,649

(22) Filed: Dec. 1, 2017

(65) Prior Publication Data

US 2018/0153564 A1 Jun. 7, 2018

Related U.S. Application Data

(60) Provisional application No. 62/428,584, filed on Dec. 1, 2016, provisional application No. 62/437,272, filed on Dec. 21, 2016.

(51) Int. Cl.
*A61B 17/17* (2006.01)
*A61F 2/08* (2006.01)
*A61B 90/00* (2016.01)

(52) U.S. Cl.
CPC ...... *A61B 17/1714* (2013.01); *A61B 17/1764* (2013.01); *A61F 2/0811* (2013.01); *A61B 2090/034* (2016.02); *A61B 2090/067* (2016.02)

(58) Field of Classification Search
CPC .................... A61B 17/1714; A61B 17/1764

USPC ............................................. 606/96
See application file for complete search history.

(56) References Cited

U.S. PATENT DOCUMENTS

| | | | |
|---|---|---|---|
| 5,154,720 | A | 10/1992 | Trott et al. |
| 5,163,940 | A | 11/1992 | Bourque |
| 8,668,738 | B2 | 3/2014 | Schmieding et al. |
| 8,685,033 | B2 | 4/2014 | Johnson et al. |

(Continued)

FOREIGN PATENT DOCUMENTS

| | | |
|---|---|---|
| DE | 20019026 U1 | 3/2002 |
| EP | 2409656 A1 | 1/2012 |

OTHER PUBLICATIONS

International Search Report and Written Report for International Application No. PCT/US2017/063956 dated Feb. 6, 2018.

*Primary Examiner* — Si Ming Ku
(74) *Attorney, Agent, or Firm* — Burns & Levinson, LLP; Joseph M. Maraia; Marlo Schepper Grolnic (57) ABSTRACT

A drill guide system provides a means of improved tunnel placement accuracy by allowing the drill guide to articulate to seat against the bone being drilled. The drill guide includes an articulating drill guide adapter constructed in four parts: a top cap, a thumbscrew, a lock tab, and a spring mechanism. The drill guide adapter is part of an aimer arm which mates with a handle on the proximal end and an aimer guide on the distal end. The drill guide adaptor allows the aimer guide to articulate relative to an irregular mating surface, allowing for increased area contact between the aimer guide template and bone. Examples of the drill guide adaptor also include a means for locking the aimer guide into place relative to the aimer arm.

16 Claims, 8 Drawing Sheets

(56) References Cited

U.S. PATENT DOCUMENTS

| | | | |
|---|---|---|---|
| 8,690,885 B2* | 4/2014 | Smith | A61B 17/1714 |
| | | | 606/96 |
| 2012/0123417 A1 | 5/2012 | Smith | |
| 2012/0330321 A1* | 12/2012 | Johnson | A61B 17/1764 |
| | | | 606/96 |
| 2013/0012945 A1 | 1/2013 | Chreene et al. | |
| 2016/0089159 A1 | 3/2016 | Ardito et al. | |
| 2016/0089160 A1 | 3/2016 | Ardito et al. | |

* cited by examiner

SURGICAL DRILL GUIDE SYSTEM WITH ARTICULATING GUIDE ADAPTOR

CROSS-REFERENCE TO RELATED APPLICATIONS

This application claims priority to and benefit of U.S. Provisional Application No. 62/428,584, filed Dec. 1, 2016, entitled ARTICULATING DRILL GUIDE, and to U.S. Provisional Application No. 62/437,272, filed Dec. 21, 2016, entitled SURGICAL DRILL GUIDE SYSTEM WITH ARTICULATING GUIDE ADAPTOR, the contents of which are incorporated by reference herein in their entirety for all purposes.

FIELD

The present disclosure relates generally to surgical drill guides. More specifically, the present disclosure relates to surgical drill guides for the positioning and orienting of holes to be drilled in a femur during ACL reconstruction.

BACKGROUND

Reconstructive surgery often involves drilling into bone to attach soft tissue such as ligament and tendon grafts, as well as various artificial replacements and/or attachments, for articulated joints. In particular, reconstructive surgery involving the anterior cruciate ligament (ACL) of the knee is becoming particularly significant because the effectiveness of reconstruction can have a profound effect on the subsequent mobility of the patient. Similarly, an improperly treated ACL injury can be a permanent detriment.

A damaged ACL is often replaced with a graft from a patellar tendon or a semitendinosus tendon. Such a repair is facilitated by tunnels formed in the tibia and/or femur for use in implanting the graft in the patient's knee. The graft may then be secured in the tunnels by fixation means, such as interference screws or sutures tied to screw posts. The femur, in particular, because it often bears the entire weight of the patient, and being the largest human bone, may be relied upon to accommodate a substantial connective force from a surgically added structure. Attachment of grafts, therefore, is often performed at a structurally sound location on the femur.

Typically, when performing an outside-in drilling procedure, a drill guide adapted for insertion into the knee joint locates a drilling exit point on the femur, while a surgeon manipulates the handle of the drill guide to locate an entry location. However, conventional drill guides for directing placement of the drilled hole are universal, using a single design having a fixed relationship between an aimer arm and a handle to identify a point of drilling. Conventional approaches, therefore, do not distinguish a left from right knee, nor individual differences in the bone configuration of an individual patient, which compromises the ability to locate an optimal entry point for drilling. Surgeons may attempt a similar range of application by employing fixed left and right guides, or a series of fixed angle guides for both right and left application. However, this results in a trial and error administration as well as requiring the manufacturing of a range of multiple fixed angle guides.

SUMMARY

Disclosed herein is a surgical drill guide system that provides a means of improved tunnel placement accuracy by allowing the drill guide to articulate to seat against the bone being drilled. The drill guide includes an articulating guide adapter constructed in four parts: a top cap, a thumbscrew, a lock tab, and a spring mechanism. The guide adapter is part of an aimer arm which mates with a handle on the proximal end and an aimer guide on the distal end. The guide adaptor allows the aimer guide to articulate relative to an irregular mating surface, allowing for increased area contact between the aimer guide template and bone. Examples of the guide adaptor also include a means for locking the aimer guide into place relative to the aimer arm. The guide adaptor of this disclosure could also be adapted for use with non-circular, or modular, drill guides.

Advantageously, the drill guide system of this disclosure substantially overcomes the above-described shortcomings by employing the guide adaptor to pivot the aimer guide for positioning a femoral or tibial tunnel. Locating the drilling hole for placement of the tunnel optimally penetrates a minimal depth of soft tissue (skin, muscle, etc.) yet directs drilling into a sufficiently rigid and structurally sound area of the femur. The guide adaptor allows placement of the aimer guide template at a desired drilling exit location on the femur. Moreover, the handle includes a sleeve member indicative of the drilling location, and a surgeon may manipulate the handle by pivoting the handle around the guide adaptor to place the sleeve at an optimal drilling location while maintaining the same exit location defined by the aimer guide template. In this manner, an optimal drilling location is selectable by positioning the handle to an area of minimal soft tissue depth and in line with a structurally sound path through the femur.

Further examples of the surgical drill guide system of this disclosure may include one or more of the following, in any suitable combination.

In examples, the surgical drill guide system of this disclosure includes a handle having an aperture extending through a proximal portion thereof for maintaining slideable communication with a sleeve member along an insertion axis. The sleeve member is elongated and has a tip. The system also includes an arm slidably engaging a slot in a distal portion of the housing for arcuate movement thereto. The arm has a proximal end engaging the slot and a distal end including an open bore. The system also includes a rotating member having a threaded shaft extending through a hole in a locking member and at least partially through the bore of the arm, and a biasing member disposed between the locking member and the bore of the arm. The biasing member is configured to bias the locking member and the rotating member away from the bore in the arm. The system yet further includes a guide removably coupled to the shaft of the rotating member and extending from the rotating member towards the insertion axis, and a template formed integrally with a distal end of the guide. The template has an aperture defining a drilling footprint corresponding to a bone tunnel through which a surgical attachment is passed. The locking member further includes a locking mechanism for locking the guide at a degree of rotation about a hinge axis defined by the shaft of the rotating member.

In further examples of the surgical drill guide system of this disclosure, a surface of the sleeve member has teeth for selective ratcheting engagement with an interior portion of the handle when the sleeve member rotated. The tip of the sleeve member includes an engaging edge for fixing the sleeve against bone. The sleeve is configured for passage of a guide wire. A surface of the arm has at least one marking for measuring arcuate extension of the arm relative to the handle. The bore of the arm defines a shelf for housing the biasing member. In examples, the rotating member is a thumbwheel. In other examples, the biasing member is a spring disposed around the shaft of the rotating member. In further examples, a cap member is fixedly attached to the arm, and the biasing member biases the locking member and the rotating member towards the cap member. The guide includes an internally threaded portion for coupling to the shaft of the rotating member.

In yet further examples, the locking mechanism includes a pin on the locking member for selective engagement with a plurality of depressions formed in the arm. In other examples, the locking mechanism includes a plurality of spines on the locking member for selective engagement with a plurality of splines formed in the arm. A surface of the arm housing the bore includes a recess for limiting a range of articulation of the guide, the range of articulation being about 25 degrees. The locking member includes a tail feature for engagement with a pocket formed in the shelf for limiting a range of articulation of the guide, the range of articulation being about 25 degrees.

Examples of a method for surgical drilling of this disclosure include: 1) deploying an arm of a handle of a drill guide to a pre-selected location, the arm engaging with a slot in a distal portion of the handle for arcuate movement therein; 2) pivoting a rotating member securing an aimer guide to a distal end of the arm about a hinge axis defined by a shaft of the rotating member, the shaft extending through an opening in a locking member, the aimer guide having a template formed integrally with a distal end of the aimer guide from the rotating member; 3) disposing the template at a placement point along an insertion axis defined by a sleeve member, the sleeve member slidably extending through a proximal portion of the handle and configured for passage of a guide wire, the hinge axis and the insertion axis intersecting for defining the placement point representative of a drilling site along the insertion axis; 4) advancing a tip of the sleeve member to the drilling site; and 5) passing the guide wire through the sleeve member to indicate a path for a surgical drill. The method further includes releasing a locking mechanism, the locking mechanism locking the aimer guide at a selected angular position relative to the arm. In examples, the locking mechanism has a pin on the locking member for selective engagement with a plurality of depressions formed in the arm. In other examples, the locking mechanism has a plurality of spines on the locking member for selective engagement with a plurality of splines formed in the arm.

Examples of a device for use with a surgical drill guide of this disclosure include a cap member fixedly attached to an arm of a drill guide. The device also includes a rotating member having a threaded shaft extending through a hole in a locking member and at least partially through a bore in the arm. A biasing member is disposed between the locking member and the bore, the biasing member configured to bias the locking member and the rotating member towards the cap member. The device also includes a guide removably coupled to the shaft of the rotating member. The rotating member rotates the guide relative to the arm about a hinge axis defined by the shaft of the rotating member. In further examples of the device, the locking member comprises a locking mechanism for locking the guide at a degree of rotation about the hinge axis. In examples, the locking mechanism includes a pin on the locking member for selective engagement with a plurality of depressions formed in the arm. In other examples, the locking mechanism includes a plurality of spines on the locking member for selective engagement with a plurality of splines formed in the arm.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

In the description that follows, like components have been given the same reference numerals, regardless of whether they are shown in different examples. To illustrate example (s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Discussed below is an example configuration and deployment of the surgical drill guide system of this disclosure. In an example arrangement, an ACL repair employing the surgical drill guide system for femoral drilling is shown. Alternate configurations may employ placement on other skeletal structures, or on softer tissue surfaces, and may or may not employ a drilling approach for excavating the insertion tunnel for a guidewire.

Figure 1A:
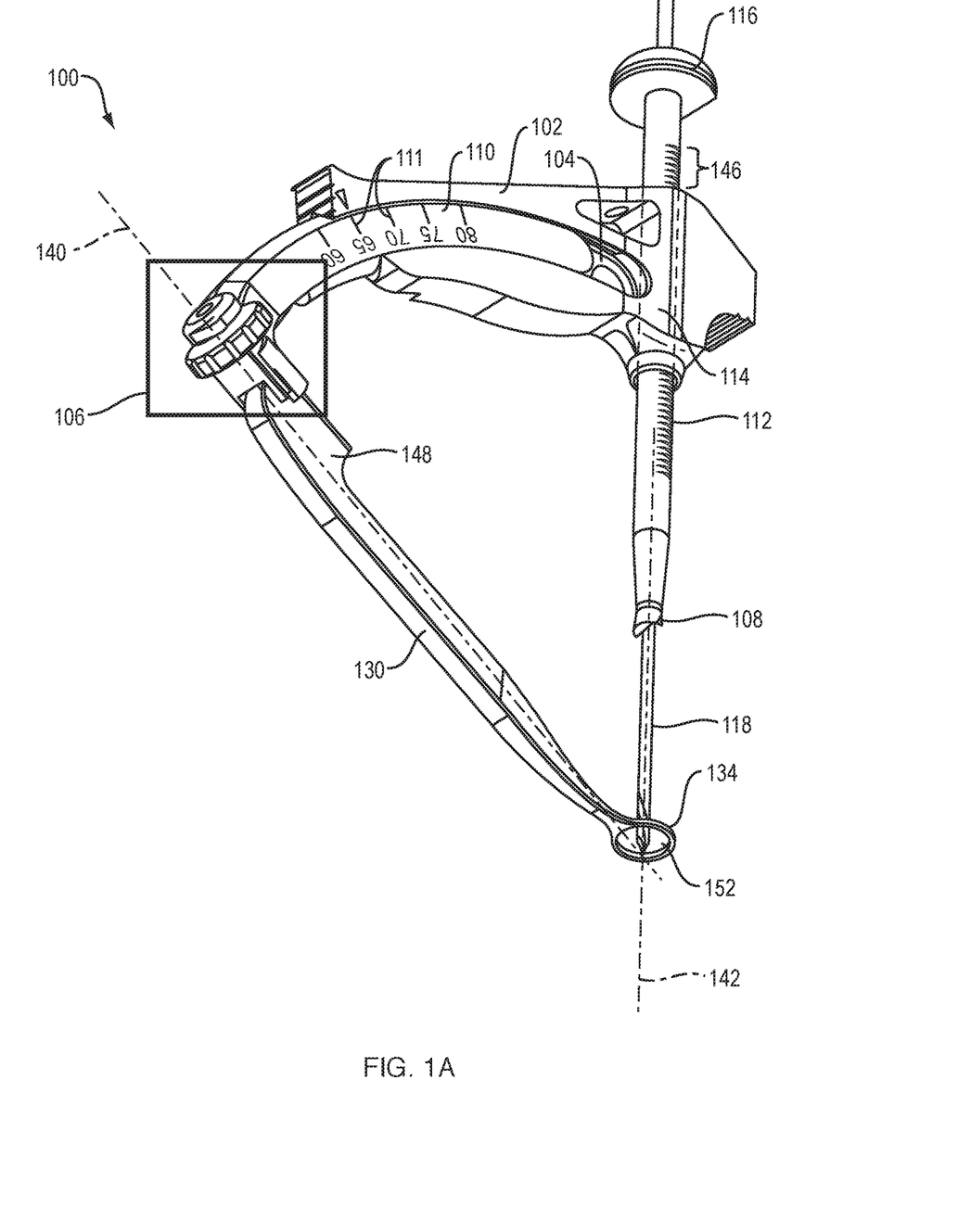
FIG. 1A shows a perspective view of an exemplary surgical drill guide system as disclosed herein.
Figure 1B:
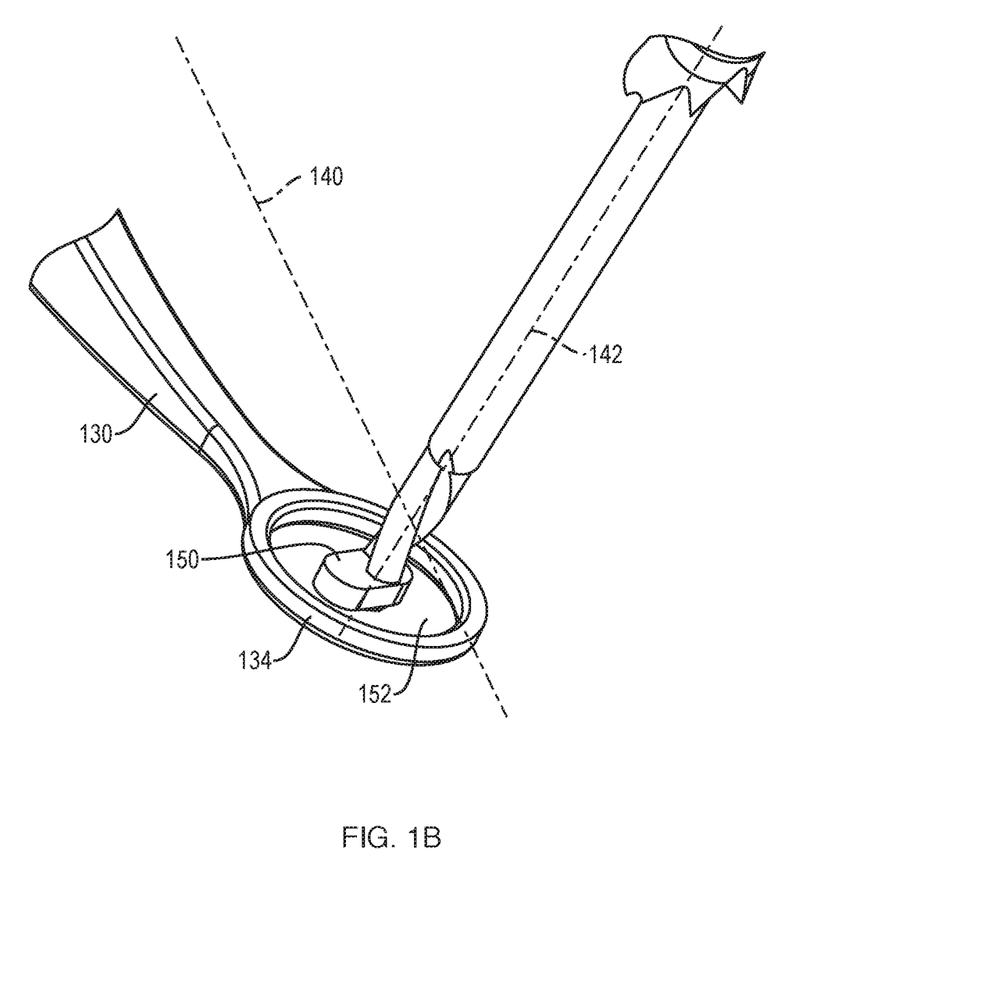
FIG. 1B shows a detailed view of the intersection between the sleeve and the aimer guide of the surgical drill guide system of FIG. 1A.

Turning now to FIG. 1A, a perspective view of an exemplary surgical drill guide system 100 of this disclosure is shown. In FIG. 1A, the surgical drill guide system 100 includes a handle 102 having an arc-shaped slot 104. The handle 102 is shaped for a secure grasp by a surgeon or other operator. An aimer arm 110 is configured to slideably engage with the slot 104 in the handle 102 for arcuate movement relative to the handle 102. A surface of the aimer arm 110 includes tick markings 111 for measuring the arcuate extension of the aimer arm 110. The aimer arm 110 terminates in a guide adaptor 106, described in more detail below. The guide adaptor 106 is configured to secure an aimer guide 130 to the aimer arm 110. The guide adaptor 106 also adapts the aimer guide 130 for rotation about a hinge axis 140, within a range of approximately 25 degrees. The aimer guide 130 has an internally-threaded side portion 148 for engagement with the guide adaptor 106, as further described below. The aimer guide 130 also includes a template 134 formed at the distal end of aimer guide 130 from the guide adaptor 106. The template 134 includes an aperture 152 defining a drilling footprint at a surgical site. The aimer guide 130 is removeably interchangeable with other aimer guides 130 having different sized apertures 152, thus the aimer guide 130 has a range of configurations for selecting aperture sizes.

Still referring to FIG. 1A, the surgical drill guide system 100 also includes a sleeve 112 disposed through an aperture 114 in the handle 102 and configured for passage of a guide wire 118. The sleeve 112 is adapted for slideable movement within the aperture 114 along an insertion axis 142. A surface of the sleeve 112 includes slanting teeth 146 for selective ratcheting engagement with a pawl (not shown) disposed within the handle 102 when the sleeve 112 is rotated via an insertion knob 116 such that the teeth 146 engage the pawl. The sleeve 112 is extendable along the insertion axis 142 through a range from the aperture 114 in the handle 102 to the template 134 to define a drilling and/or insertion hole for the guide wire 118. A taper, serration, or other suitable engaging edge on the tip 108 of the sleeve 112 facilitates the fixing of the sleeve 112 against bone or another hard surface. Typically, a soft tissue incision is made where the tip 108 contacts soft tissue, and the sleeve 112 inserted until hard material (i.e. bone) is encountered. The tip 108 engages the bone facilitated by the ratcheting action of the teeth 146 to avoid slippage during insertion of the guide wire 118.

It should be noted that, when the aimer guide 130 is centered on the guide adaptor 106, as shown in FIG. 1A, the insertion axis 142 is aligned with the center of the aperture 152 of the template 134. However, when the aimer guide 130 is rotated about the hinge axis 140 to its extreme angular limits, the insertion axis 142 is slightly offset from the center of the aperture 152. As shown in more detail in FIG. 2, the hinge axis 140 does not pass through the center of the aperture 152. Thus, the target shape that the guide wire 118 traces as the aimer guide 130 is adjusted from one angular extreme to the other is represented by the oval target 150.

Figure 2:
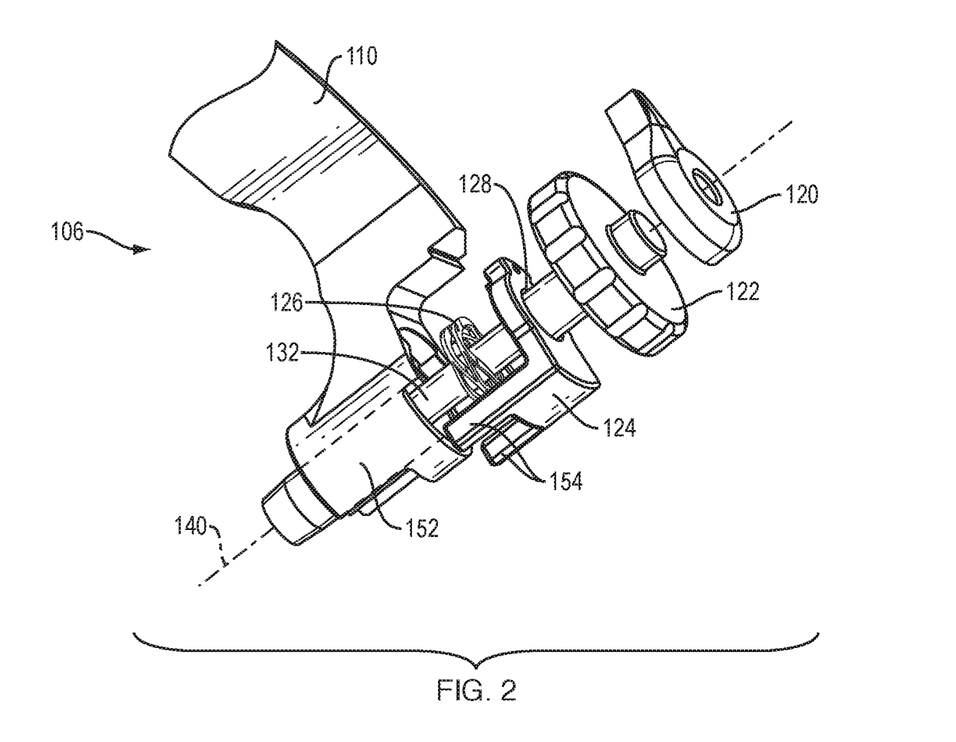
FIG. 2 shows a detailed view of the guide adaptor of the surgical drill guide system of FIG. 1A.

FIG. 2 is a semi-exploded detailed view of the distal end of the aimer arm 110, including the component parts of the guide adaptor 106. The guide adaptor 106 generally comprises four elements: a top cap 120; a rotating member, such as a thumbwheel 122; a lock tab 124; and a biasing member, such as a spring 126. The top cap 120 is rigidly connected to the aimer arm 110. The lock tab 124 has an aperture 128 for slidable passage of a shaft 132 of the thumbwheel 122. The shaft 132 extends through an open bore 152 in the distal end of the aimer arm 110. The spring 126 is slidably disposed around the shaft 132 and is configured to urge the lock tab 124 and the thumbwheel 122 toward the top cap 120. In other words, the thumbwheel 122, the lock tab 124, and the spring 126 are held together by being sandwiched between the bore 152 in the aimer arm 110 and the top cap 120.

In examples, the distal end of shaft 132 is threaded to engage the internal threads of the side portion 148 of the aimer guide 130 (FIG. 1A) when the aimer guide 130 is positioned between two extending stops 154 on the lock tab 124. However, it is contemplated by this disclosure that the shaft 132 and the aimer guide 130 could also be coupled by other means, such as a quick-release toggle lock having a tapered end in the shaft 132 which mates with a corresponding taper in the aimer guide 130. Thus, by rotation of the thumbwheel 122, the guide adaptor 106 pivots the aimer guide 130 relative to the aimer arm 110 along the hinge axis 140.

In examples, the aimer guide 130 can furthermore be locked into position at a selected angle relative to the aimer arm 110 by means of a locking mechanism in the guide adaptor 106. A range of motion of the aimer guide 130 can also be limited by certain features of the guide adaptor 106. Examples of these locking mechanisms and limiting features will now be described with regard to FIGS. 3A-5B.

Figure 3A:
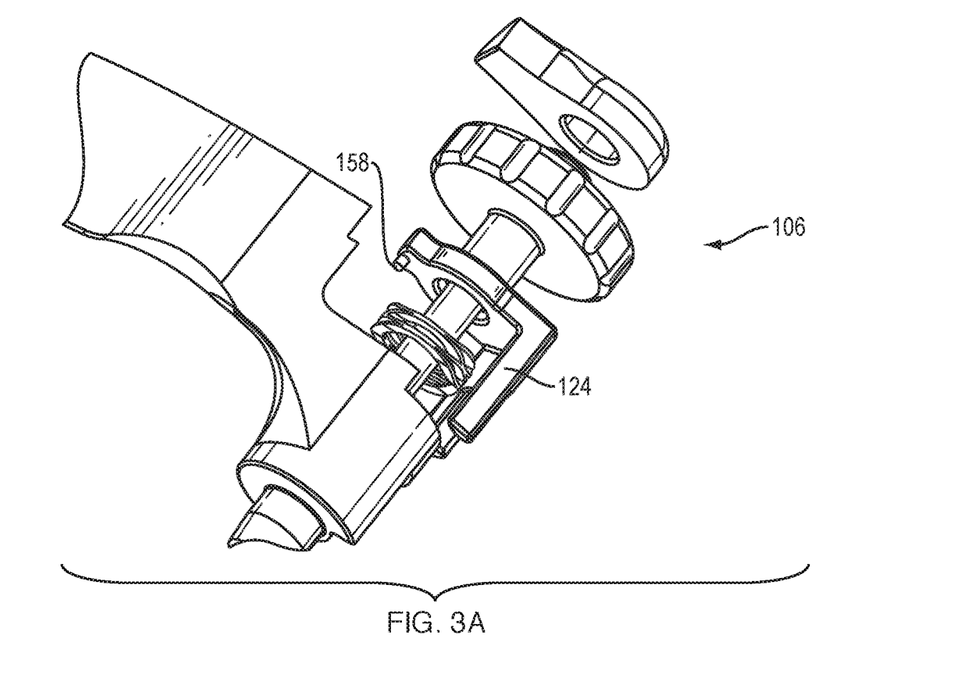
FIGS. 3A-3C illustrate an exemplary locking mechanism of the guide adaptor of FIG. 2.
Figure 3B:
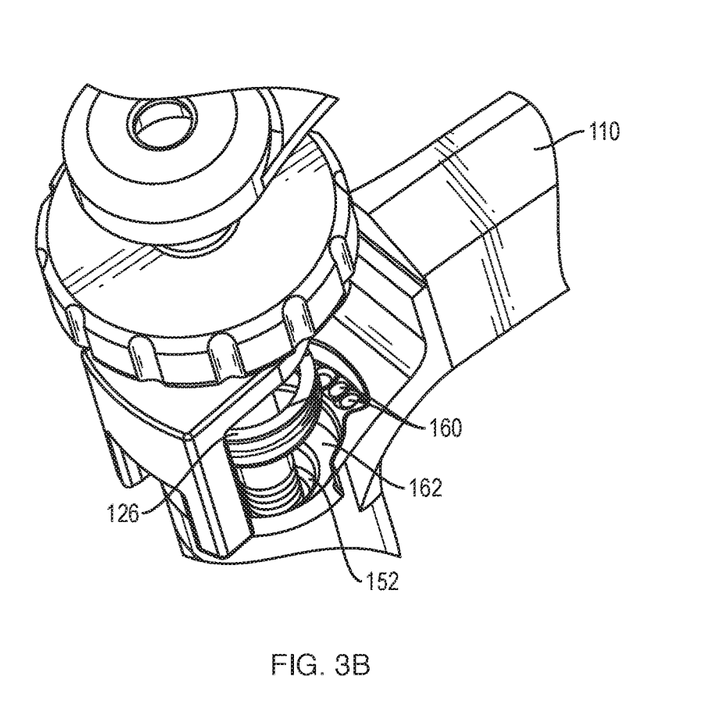
Figure 3C:
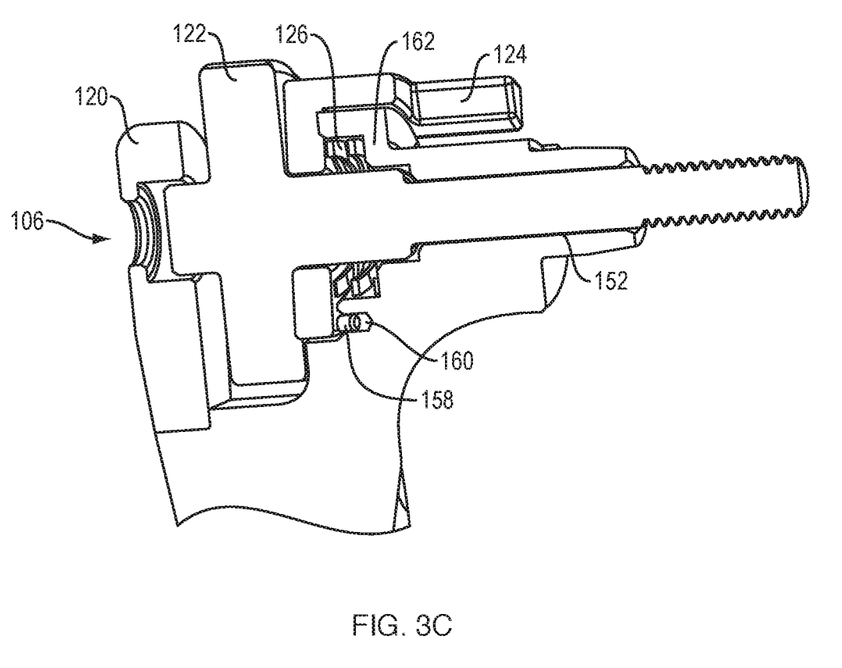

A first example of a locking mechanism will now be described with regard to FIGS. 3A-3C. In FIG. 3A it can be seen that the lock tab 124 comprises a tapered pin 158 that is received into a mating depression 160 in the aimer arm 110, shown in FIG. 3B. In FIG. 3B, it can also be seen that the bore 152 is stepped to include a shelf 162 for housing the spring 126. A number of depressions 160 exist in the aimer arm 110 for receiving the tapered pin 158, based on the desired angular placement of the aimer guide 130. A cross-sectional view of the locked guide adaptor 106 is shown in FIG. 3C. The lock tab 124, the spring 126 and the thumbscrew 122 are shown as trapped between the shelf 162 in the bore 152 and the top cap 120. When the thumbwheel 122 is tightened, the tapered pin 158 engages the depression 160 in the arm, preventing the lock tab 124 from rotating, and thus the aimer guide 130 from articulating. Conversely, when the thumbwheel 122 is loosened, the spring 126 urges the lock tab 124 away from the bore 152 to release the tapered pin 158 from the depression 160, allowing limited articulation of the aimer guide 130.

Figure 4:
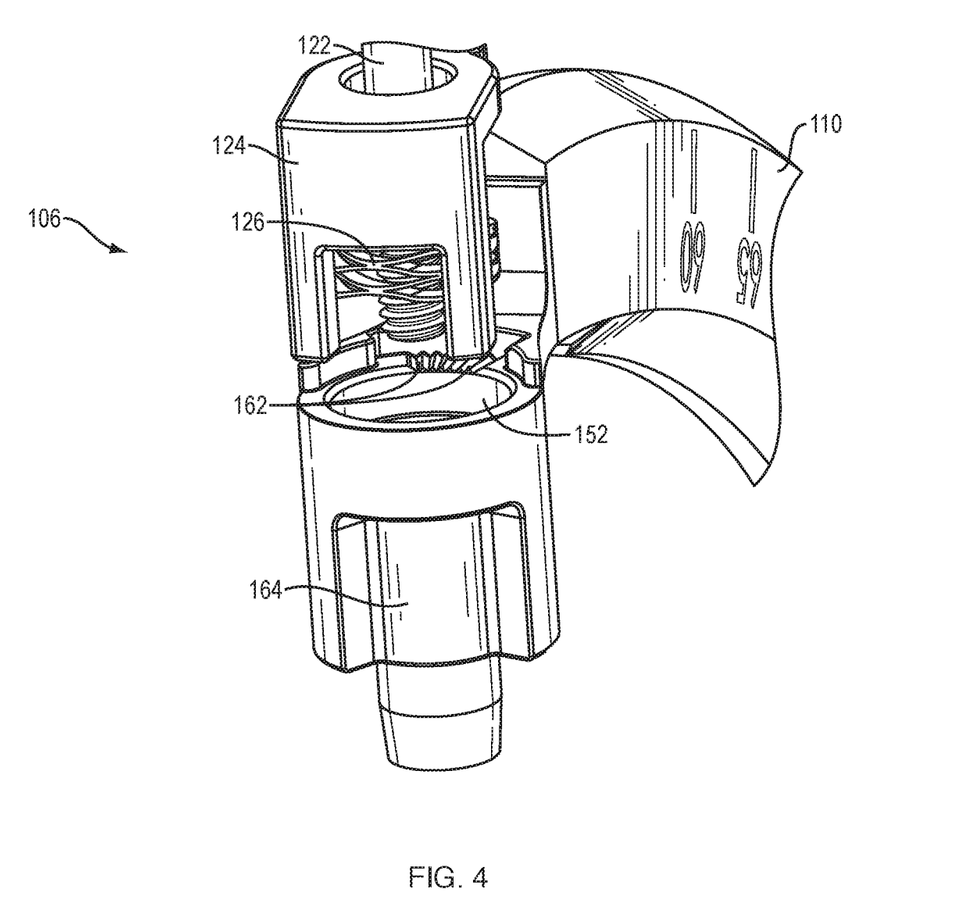
FIG. 4 illustrates an alternative locking mechanism of the guide adaptor of FIG. 2.
Figure 5A:
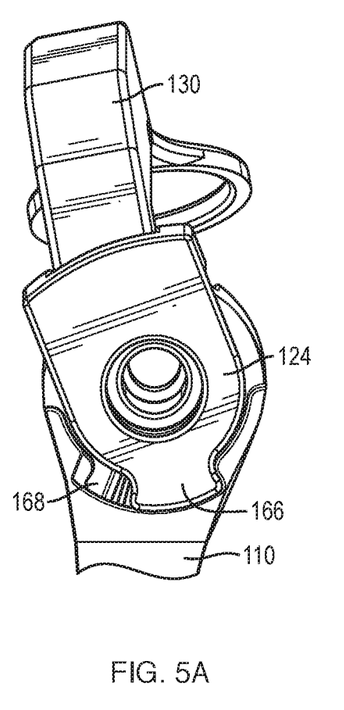
FIGS. 5A and 5B illustrate an exemplary articulation limiter of the guide adaptor of FIG. 4.
Figure 5B:
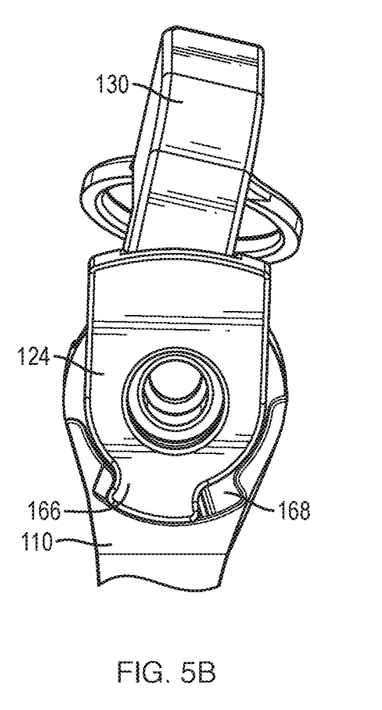

An alternative example of a locking mechanisms is shown in FIG. 4. In FIG. 4, instead of a number of depressions 160 as in FIG. 3B, a number of splines 162 exist in the aimer arm 110 for receiving corresponding spines (not shown) on the underside of the lock tab 124, based on the desired angular placement of the aimer guide 130. The splines 162, when engaged, allow the aimer guide 130 to lock in discrete articulation steps. When the thumbwheel 122 is tightened, the splines 162 mesh with the spines on the underside of the lock tab 124, preventing the lock tab 124 from rotating, and thus the aimer guide 130 from articulating. Conversely, when the thumbwheel 122 is loosened, the spring 126 urges the lock tab 124 away from the bore 152 to release from the splines 162, allowing limited articulation of the aimer guide 130.

In addition to the locking mechanisms shown in FIGS. 3A, 3B and 4, other suitable locking mechanisms between the lock tab 124 and the aimer arm 110 are also contemplated by this disclosure. For example, a radial locking mechanism could be used instead of the face-locking mechanisms described above. It is contemplated that a splined shaft 132 of the thumbwheel 122 could be used in such a locking mechanism.

In FIG. 4, it can also be seen that a surface of the portion of the aimer arm 110 housing the bore 152 also includes a recess 164 which limits the range of the articulation of the aimer guide 130. The recess 164 can be applied to all examples of the guide adaptor 106 and is not limited to the example shown in FIG. 4. Further examples of articulation limiters are shown with regard to FIGS. 5A and 5B. In these examples, the lock tab 124 includes a tail feature 166 that serves as a stop mechanism when the elevation of the lock tab 124 relative to the shelf 162 of the aimer arm 110 (FIG. 3B) causes the tail feature 166 to engage with a pocket 168 created in the shelf 162 of the aimer arm 110. The pocket 168 thus restricts the angular rotation of the lock tab 124. This mechanism provides an additional means to restrict the articulation of the aimer guide 130 within a desired range. The tail feature 166 can be applied to all examples of the guide adaptor 106 and is not limited to the example shown in FIG. 4.

Figure 6:
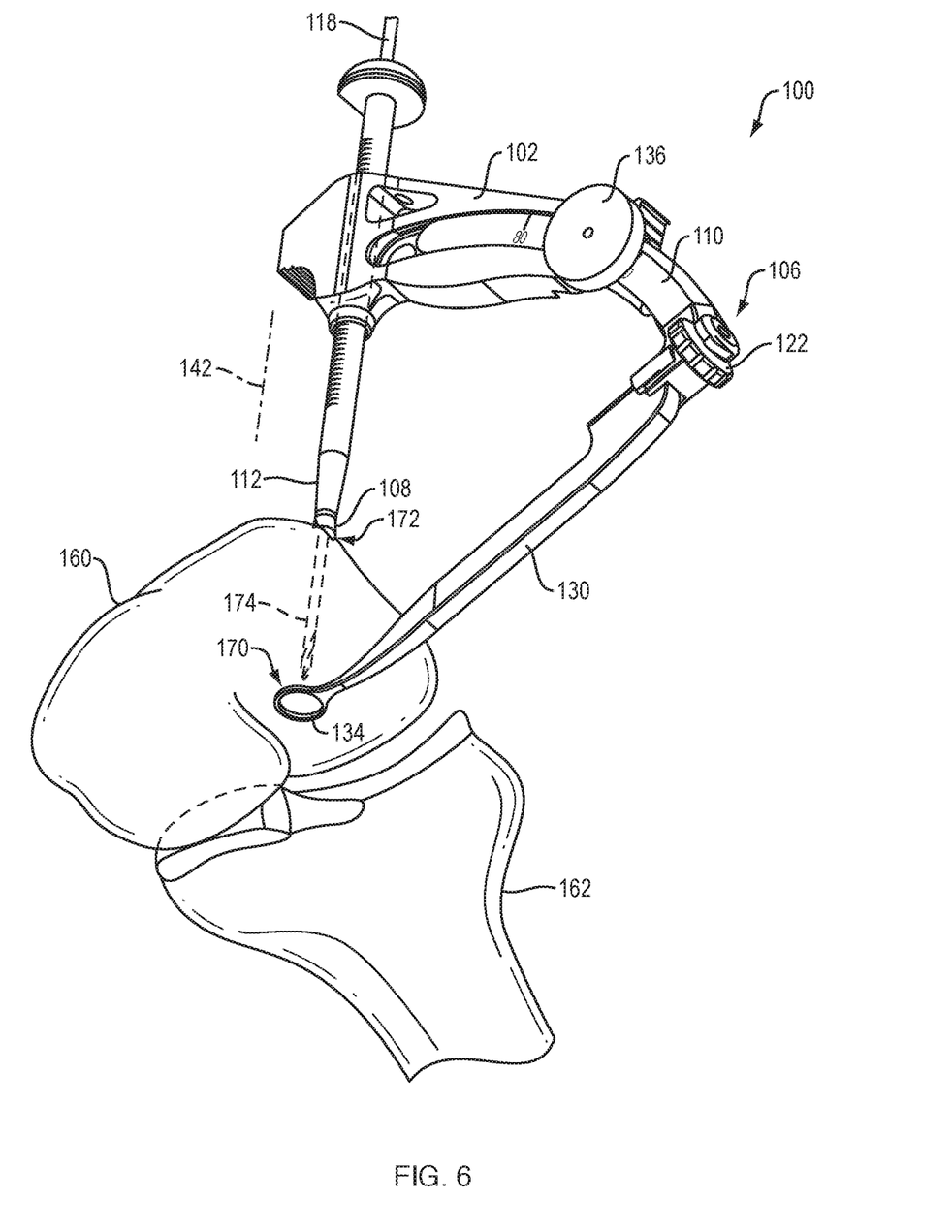
FIG. 6 illustrates an exemplary method for surgical drilling employing the surgical drill guide system of FIG. 1A.

In FIG. 6, a method for surgical drilling using an exemplary surgical drill guide system 100 of this disclosure is illustrated. FIG. 6 shows the surgical drill guide system 100 disposed at a surgical site comprising a femur 160 and a tibia 162. To begin the method, a surgeon or other operator deploys the aimer arm 110 of the handle 102 to a suitable location for drilling as defined by a drilling site 172. Once deployed, the aimer arm 110 may be locked into place relative to the handle 102 by a knob 136 or other suitable feature on the handle 102. The surgeon then releases the locking mechanism of the guide adaptor 106 by loosening the thumbwheel 122 and pivots the aimer guide 130 by rotating the thumbwheel 122. By rotating the thumbwheel 122, the surgeon then disposes the template 134 at a placement point 170 on the femur 160. Typically, the placement point 170 would be the same location as the prior attachment point of the ligament being repaired, but other suitable locations may be determined. The surgeon then disposes the sleeve 112 such that the sleeve 112 is slideably movable through the handle 102. The tip 108 of the sleeve 112 is then advanced to the drilling site 172, such as an anatomically sound location on the femur 160. This allows marking and fixing, via the edge at the tip 108 of the sleeve 112, a drilling site 172 for insertion of the guide wire 118. It is notable that the placement point 170 for the template 134 defines location along the insertion axis 142 for insertion of the guidewire 118 towards the drilling site 172. The tip 108 of the sleeve 112 passes through soft tissue (not shown) and contacts the drilling site 172 at the bone, cartilage, or other hard surface underneath the soft tissue. A drill (not shown) may subsequently be employed to further excavate an insertion tunnel 174 from the drilling site 172 towards the placement point 170 of the template 134.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting, the full scope rather being conveyed by the appended claims.

What is claimed is:

1. A surgical drill guide system comprising:
a handle having an aperture extending through a proximal portion thereof for maintaining slideable communication with a sleeve member along an insertion axis, the sleeve member being elongated and having a tip;
an arm slidably engaging a slot in a distal portion of a housing for arcuate movement thereto, the arm having a proximal end engaging the slot and a distal end including an open bore;
a rotating member having a threaded shaft extending through a hole in a locking member and at least partially through the bore of the arm;
a biasing member disposed between the locking member and the bore of the arm, the biasing member configured to bias the locking member and the rotating member away from the bore in the arm;
a guide removably coupled to the shaft of the rotating member and extending from the rotating member towards the insertion axis; and
a template formed integrally with a distal end of the guide, the template having an aperture defining a drilling footprint corresponding to a bone tunnel through which a surgical attachment is passed;
wherein the locking member comprises a locking mechanism for locking the guide at a degree of rotation about a hinge axis defined by the shaft of the rotating member.

2. The system of claim 1, wherein a surface of the sleeve member comprises teeth for selective ratcheting engagement with an interior portion of the handle when the sleeve member rotated.

3. The system of claim 1, wherein the tip of the sleeve member comprises an engaging edge for fixing the sleeve against bone.

4. The system of claim 1, wherein the sleeve is configured for passage of a guide wire.

5. The system of claim 1, wherein a surface of the arm comprises at least one marking for measuring arcuate extension of the arm relative to the handle.

6. The system of claim 1, wherein the bore of the arm defines a shelf for housing the biasing member.

7. The system of claim 1, wherein the rotating member is a thumbwheel.

8. The system of claim 1, wherein the biasing member is a spring disposed around the shaft of the rotating member.

9. The system of claim 1, further comprising a cap member fixedly attached to the arm, the biasing member biasing the locking member and the rotating member towards the cap member.

10. The system of claim 1, wherein the guide comprises an internally threaded portion for coupling to the shaft of the rotating member.

11. The system of claim 1, wherein the locking mechanism comprises a pin on the locking member for selective engagement with a plurality of depressions formed in the arm.

12. The system of claim 1, wherein the locking mechanism comprises a plurality of spines on the locking member for selective engagement with a plurality of splines formed in the arm.

13. The system of claim 1, wherein a surface of the arm housing the bore comprises a recess for limiting a range of articulation of the guide.

14. The system of claim 13, wherein the range of articulation is about 25 degrees.

15. The system of claim 1, wherein the locking member comprises a tail feature for engagement with a pocket formed in a shelf for limiting a range of articulation of the guide.

16. The system of claim 15, wherein the range of articulation is about 25 degrees.

\* \* \* \* \*